United States Patent [19]

Haber

[11] Patent Number: 4,799,926

[45] Date of Patent: Jan. 24, 1989

[54] SYRINGE, HAVING SELF-CONTAINED, STERILE, MEDICATION APPLYING SWAB

[75] Inventor: Terry M. Haber, Lake Forest, Calif.

[73] Assignee: Habley Medical Technology Corporation, Laguna Hills, Calif.

[21] Appl. No.: 107,676

[22] Filed: Oct. 13, 1987

[51] Int. Cl.⁴ .............................................. A61M 5/00
[52] U.S. Cl. ................................... 604/187; 604/199; 604/1
[58] Field of Search .................. 604/1, 187, 194, 195, 604/196, 199

[56] References Cited

U.S. PATENT DOCUMENTS

| | | | |
|---|---|---|---|
| 1,499,508 | 7/1924 | Deane | 604/194 |
| 3,270,743 | 9/1966 | Gingras | 604/199 X |
| 4,243,035 | 1/1981 | Barrett | 604/1 |

Primary Examiner—John D. Yasko
Attorney, Agent, or Firm—Morland C. Fischer

[57] ABSTRACT

A syringe having a self-contained, sterile, medication impregnated swab by which to apply an anesthetic and/or antiseptic to a targeted tissue area of a patent prior to the administration of an injection at the target site. The swab is carried by and extended through the major flange of a hollow piston stem. A rotatable end cap is pivotally attached to the piston flange to surround the swab and preserve the sterility thereof. After the cap has been opened, the targeted tissue area swabbed, and an injection administered, an elongated body (the protective sheath which initially surrounds the needle cannula to preserve the sterility thereof and prevent an accidental needle strike) is inserted into and pushed distally through the interior of the hollow piston stem to correspondingly drive the swab therewithin. Accordingly, the swab is conveniently, safely and permanently retained within the hollow piston stem to be discarded with the syringe, after use.

11 Claims, 1 Drawing Sheet

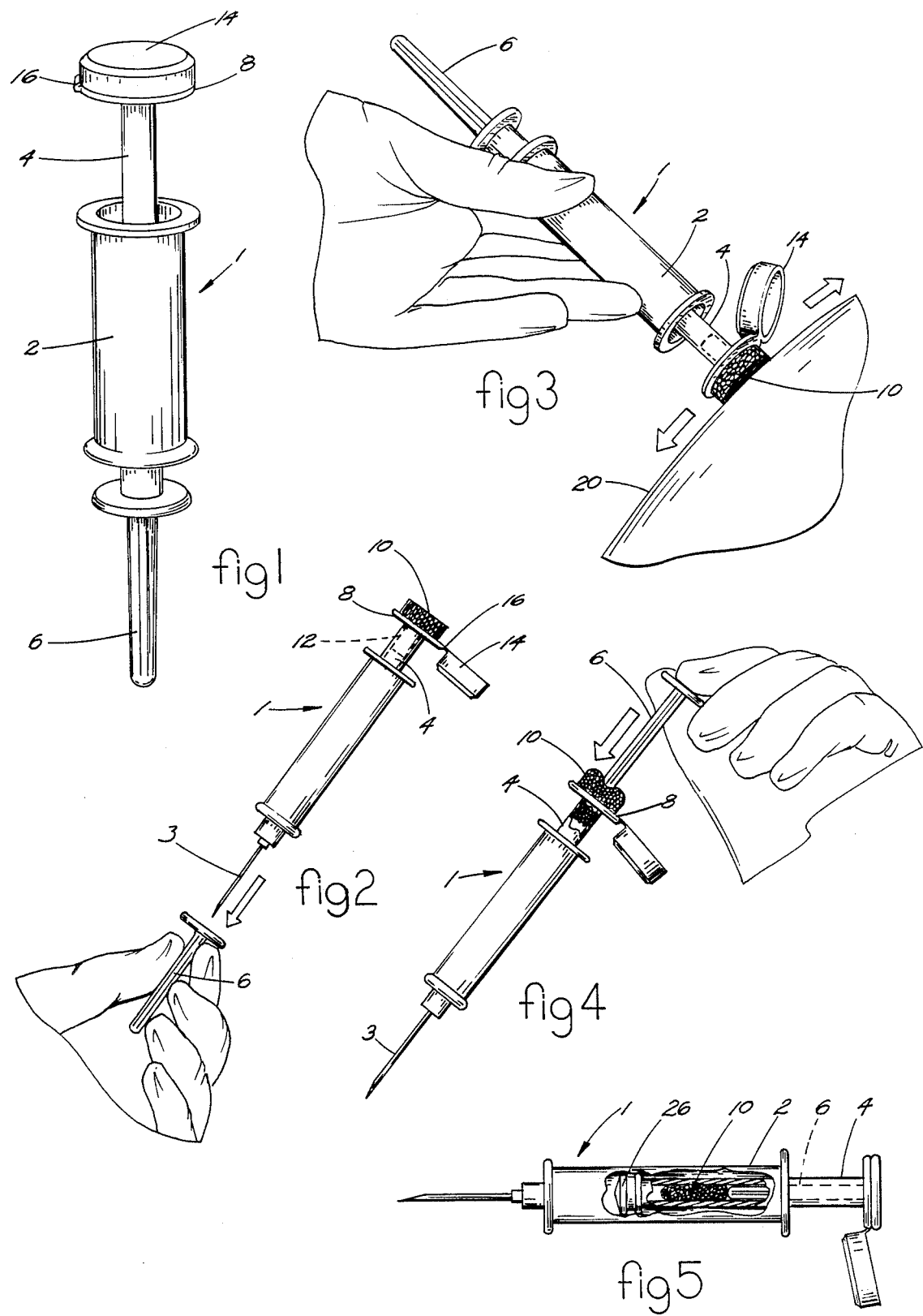

SYRINGE, HAVING SELF-CONTAINED, STERILE, MEDICATION APPLYING SWAB

BACKGROUND OF THE INVENTION

1. Field of the Invention

This invention relates to a syringe having a self-contained, pre-sterilized, medication impregnated swab by which to apply medication to a targeted tissue area of a patent prior to the administration of an injection at the target site.

2. Prior Art

It is a universally accepted procedure among health care workers to apply a local anesthetic and/or an antiseptic to a tissue area of a patent just prior to the administration of an injection. The medication is typically applied by means of a (usually sterile) cotton swab which must first be adequately saturated. However, because the cotton swab is handled by a health care worker, the possibility exists that the sterile condition thereof may be jeopardized. Moreover, the cotton swab may not be sterilized in the first place. Therefore, the swab may harbor potentially infectious bacteria.

What is more, the swab be properly discarded after the patient's tissue area has been treated with medication. Failure to safely and carefully dispose of such swabs could lead to a contamination of the health care facility, and, in some cases, the spread of a life threatening disease. Consequently, the inconvenience associated with adequately saturating, properly using, and safely disposing the cotton swab, as well as the difficulty in maintaining or establishing the sterility thereof during handling, makes the conventional swab, in many cases, undesirable for use in health care facilities, particularly where maintaining a maximum sterile environment is of primary importance.

SUMMARY OF THE INVENTION

In general terms, a syringe is disclosed having a self-contained, pre-sterilized, medication impregnated swab, by which an anesthetic and/or antiseptic may be easily and reliably applied to a targeted tissue area of a patient prior to the administration of an injection at the target site. The syringe comprises a cylinder having a distally projecting needle cannula and a proximally extending, hollow piston stem. An elongated, protective sheath surrounds the needle cannula to preserve the sterility thereof and prevent an accidental needle strike. The medication impregnated swab is supported upon and extended through an opening in the major flange of the hollow piston stem. An end cap is pivotally connected to the flange of the piston stem and rotatable to either a closed position at which to surround and preserve the sterility of the swab or to an open position at which to expose the swab for applying medication to the target site.

In use, the end cap is rotated to the open position and the target site is swabbed with medication. The protective sheath is removed from the needle cannula and an injection is administered at the target site by pushing the hollow piston stem distally through the syringe cylinder to expulse the fluid contents thereof. After administration of the injection, the needle sheath is moved into contact with the swab above the major flange of the piston stem. The needle sheath is then inserted into and pushed distally through the hollow interior of the piston stem to correspondingly drive the swab therewithin. Accordingly, the swab is safely and permanently retained within the hollow piston stem to be conveniently discarded along with the syringe while avoiding the necessity of handling the swab and preventing the spread of possibly infectious bacteria.

BRIEF DESCRIPTION OF THE DRAWINGS

FIG. 1 is a plan view of the syringe which forms the present invention;

FIG. 2 shows the syringe of FIG. 1 with a needle sheath removed from a needle cannula and an end cap rotated of a presterilized, medication impregnated swab;

FIG. 3 shows the swab of FIG. 2 applying medication to a targeted tissue area prior to the administration of an injection;

FIG. 4 shows the needle sheath of FIG. 2 being inserted into a hollow piston stem of the syringe to drive the swab therewithin; and FIG. 5 shows the swab safely and permanently retained within the hollow piston stem to permit the swab to be conveniently discarded with the syringe, after use.

DESCRIPTION OF THE PREFERRED EMBODIMENT

The syringe 1 which forms the present invention and the self-contained, medication applying swab thereof are now described in detail while referring to the drawings. In FIG. 1, there is shown a syringe 1 including a hollow cylinder 2 having distal and proximal ends. Cylinder 2 includes a hypodermic needle cannula (designated 3 in FIG. 2) projecting outwardly from the distal end thereof and a hollow, reciprocating piston stem 4 extending outwardly through the proximal end for expulsing the contents of cylinder 2 via needle 3. A hollow, elongated needle sheath 6 surrounds the distally projecting end of the needle cannula to preserve the sterility thereof and prevent health care workers from being subjected to an accidental needle strike. Needle sheath 6 is detachably connected (i.e. snap-fit) to the cylinder 2 at the distal bore thereof.

The hollow piston stem 4 includes a distally oriented plunger head (designated 26 in FIG. 5) located in and movable axially through the interior of cylinder 2 and a proximally oriented major flange 8 by which to selectively control the movement and position of the plunger head through the cylinder. In accordance with the present invention, and referring concurrently to FIGS. 1 and 2 of the drawings, a pre-sterilized swab 10 (best shown in FIG. 2) is supported upon the flange 8 of piston stem 4. More particularly, the swab 10 is formed from an absorbent material (e.g. foam rubber, or the like) and is provided with a disc-like base and a coextensive, relatively narrow stem 12 (also best shown in FIG. 2). The swab 10 is impregnated with a suitable medication, such as an anesthetic or antiseptic (e.g. alcohol), which may be applied to a targeted tissue area prior to the administration of an injection. The base of swab 10 rests upon piston flange 8, while the narrow stem 12 projects through a hole (not shown) formed in the piston flange to be received by and retained within the hollow piston stem 4.

An end cap 14 is hingedly connected to the flange 8 of piston stem 4 by means of an integral hinge 16 (commonly referred to as a living hinge). Both the end cap 14 and hinge 16 are preferably formed from an impact resistant material, such as plastic, or the like. Accordingly, the end cap 14 is adapted to rotate around its hinge 16 from a closed position (of FIG. 1) to an open position (of FIG. 2). In the closed position, end cap 14 is removably attached (i.e. snap-fit) to the piston flange 8, whereby to surround and preserve the sterility of the medication impregnated swab 10. In the open position, the end cap 14 is rotated around the hinge 16 away from flange 8 to expose swab 10 and thereby permit the medication with which swab 10 is impregnated to be applied to a targeted tissue area.

Use of the syringe 1 is now described. Initially, the syringe 1 is distributed to health care workers in the configuration shown in FIG. 1. That is, the needle sheath 6 is positioned over the needle cannula 3, and the end cap 14 is rotated to the closed position, such that the sterility of both cannula 3 and swab 10 is preserved. The health care worker then rotates cap 14 to the open position (of FIG. 2), whereby to expose the swab 10. Next, and referring to FIG. 3 of the drawings, the cylinder 2 of syringe 1 is grasped with the protective sheath 6 still surrounding the needle cannula (to preserve the sterilized condition thereof and prevent an accidental needle strike). The swab 10 is located at and moved around the targeted tissue area 20 of the patient so that an adequate amount of medication will be applied from the swab to the target site.

After the targeted tissue area 20 has been swabbed with medication, the protective sheath 6 is removed to expose the needle cannula 3 (best depicted in FIG. 2) for administrating an injection at the target site. More particularly, the end cap 14 may be rotated back to the closed position, and piston stem 4 is depressed at cap 14 so as to be moved proximally through the syringe cylinder, whereby to axially advance the associated plunger head (designated 26 in FIG. 5) and expulse the contents of the cylinder. After administrating the injection, and referring to FIG. 4 of the drawings, the health care worker again rotates end cap 14 to the open position and moves the nose of needle sheath 6 (which previously surrounded needle cannula 3) into contact with the swab 10 above the major flange 8 of piston stem 4. The needle sheath 6 is inserted into and pushed distally through the hollow interior of piston stem 4 (in the direction of the reference arrow), such that the swab 10 is correspondingly driven distally through the interior of stem 4.

Accordingly, and now referring to FIG. 5 of the drawings, the swab 10 is shown pushed by needle sheath 6 through the hollow piston stem 4, at which location the swab is permanently retained. Hence, the swab 10 may be safely and conveniently discarded along with the syringe 1, after use. Moreover, by virtue of the self-contained swab 10 and the sheath 6 (which performs the dual functions of a protective needle sheath and a means for driving swab 10 through hollow piston stem 4), the health care worker never has to handle the swab. Hence, the sterility of the swab 10 is preserved and the spread of possibly infectious bacteria is avoided.

It will be apparent that while a preferred embodiment of the invention has been shown and described, various modifications and changes may be made without departing from the true spirit and scope of the invention. Having thus set forth a preferred embodiment of the invention,

What is claimed is:

1. A syringe comprising a hollow cylinder having distal and proximal ends, a hypodermic needle projecting outwardly from the distal cylinder end by which to administer an injection, a piston stem having a hollow, elongated body extending outwardly from the proximal cylinder and to be movable axially through said cylinder for expulsing the contents thereof and a flange interconnected with said body to control the movement of said stem through said cylinder, and means containing a supply of medication to be applied to a targeted tissue area of a patient prior to the administration of an injection at the target area, said medication containing means carried on the flange of said piston stem and movable into the hollow body of said stem through an opening located between said flange and said body.

2. The syringe recited in claim 1, wherein said medication containing means is an absorbent swab that is impregnated with said supply of medication.

3. The syringe recited in claim 1, further comprising a removable cap being connected to the flange of said piston stem to surround and protect said medication containing means or being removed from said flange to expose said medication containing means for applying medication to the targeted tissue area.

4. The syringe recited in claim 2, further comprising a cap pivotally connected to the flange of said piston stem and rotatable from a closed position at which to surround and protect said medication containing swab to an open position at which to expose said medication containing swab for applying medication to the targeted tissue area.

5. The syringe recited in claim 2, including means by which to drive said medication containing swab from the flange of said piston stem into the hollow body of said piston stem.

6. The syringe recited in claim 2, further comprising a needle sheath to surround and protect the distally projecting hypodermic needle, said needle sheath being removable from said needle and sized so as to be able to drive said medication containing swab from the flange of said piston stem into the hollow body of said piston stem through the opening therebetween.

7. A syringe comprising:
   a hollow cylinder having distal and proximal ends;
   a hypodermic needle projecting outwardly from the distal cylinder end by which to administer an injection;
   a hollow piston stem extending outwardly from the proximal cylinder end;
   means attached to said piston stem containing a supply of medication to be applied to a targeted tissue area of a patient prior to the administration of an injection at the target area; and
   means by which to drive said medication containing means into the hollow interior of said piston stem after medication has been applied to the targeted area.

8. The syringe recited in claim 7, wherein said piston stem has a flange surrounding the hollow body thereof by which to move said stem through said cylinder for expulsing the contents of said cylinder via said needle said medication containing means being attached to said piston stem at said flange.

9. The syringe recited in claim 8, wherein said medication containing means is an absorbent swab that is saturated with said supply of medication.

10. The syringe recited in claim 9, further comprising an end cap removably connected to the flange of said piston stem to surround and protect said medication containing swab at said flange.

11. The syringe recited in claim 7, wherein said means for driving said medication containing means into the hollow interior of said piston stem is a needle covering and protecting sheath that has been removed from said distally projecting hypodermic needle.

* * * * *